(12) United States Patent
Wangen et al.

(10) Patent No.: US 11,957,890 B2
(45) Date of Patent: Apr. 16, 2024

(54) MEDICAL DEVICE FOR INTRODUCTION OF A FLUID INTO THE BLOOD CIRCULATION SYSTEM OF A PATIENT AND METHOD FOR CONTROLLING LEAKAGE CURRENTS IN A MEDICAL DEVICE PROVIDED OR COMBINED WITH A WARMING UNIT

(71) Applicant: GAMBRO LUNDIA AB, Lund (SE)

(72) Inventors: Michael Jon Wangen, Rogers, MN (US); Daniel Edward Ruhland, Roseville, MN (US); Randy A. Miller, Lake Elmo, MN (US)

(73) Assignee: Gambro Lundia AB, Lund (SE)

( * ) Notice: Subject to any disclaimer, the term of this patent is extended or adjusted under 35 U.S.C. 154(b) by 775 days.

(21) Appl. No.: 17/256,417

(22) PCT Filed: Jun. 25, 2019

(86) PCT No.: PCT/EP2019/066878
§ 371 (c)(1),
(2) Date: Dec. 28, 2020

(87) PCT Pub. No.: WO2020/007666
PCT Pub. Date: Jan. 9, 2020

(65) Prior Publication Data
US 2021/0268205 A1    Sep. 2, 2021

(30) Foreign Application Priority Data
Jul. 2, 2018 (EP) .................................... 18181135

(51) Int. Cl.
*A61M 5/44*    (2006.01)
*A61M 1/16*    (2006.01)
(Continued)

(52) U.S. Cl.
CPC .......... *A61M 5/445* (2013.01); *A61M 1/1629* (2014.02); *A61M 1/3623* (2022.05);
(Continued)

(58) Field of Classification Search
CPC .. A61M 1/1629; A61M 1/166; A61M 1/1664; A61M 1/3623; A61M 1/369;
(Continued)

(56) References Cited

U.S. PATENT DOCUMENTS

| 4,155,852 A | 5/1979 | Fischel |
| 9,757,516 B2 | 9/2017 | Calasso |

(Continued)

FOREIGN PATENT DOCUMENTS

| CN | 103961765 | 8/2014 |
| CN | 108136097 | 6/2018 |

(Continued)

OTHER PUBLICATIONS

PCT Search Report and Written Opinion for PCT/EP2019/066878 dated Sep. 11, 2019 (13 pages).
(Continued)

*Primary Examiner* — Shefali D Patel
(74) *Attorney, Agent, or Firm* — Mueting Raasch Group

(57) ABSTRACT

A warming unit (21) coupled or configured to be coupled to a heated portion (19) of a fluid circuit (6, 7, 10, 11, 13, 14, 15; 107) of a medical device (1, 100). The warming unit (21) comprises a leakage current reduction circuit (35) configured to perform the following procedure: connecting a heat transfer element (22) of the warming unit (21) to a ground connection (33) through a resistance element (34), which keeps a normal condition patient leakage current below a first limit value, and disconnecting the heat transfer element (22) from the ground connection (33) if a current indicating that a patient is connected to a mains voltage is sensed (Continued)

through the resistance element (34), in order to keep a fault condition patient leakage current below a second limit value.

24 Claims, 4 Drawing Sheets

(51) Int. Cl.
  *A61M 1/36* (2006.01)
  *A61M 5/14* (2006.01)
(52) U.S. Cl.
  CPC ............... *A61M 1/369* (2013.01); *A61M 5/14* (2013.01); *A61M 2205/3327* (2013.01); *A61M 2205/3653* (2013.01); *A61M 2210/12* (2013.01)
(58) Field of Classification Search
  CPC ...... A61M 2205/33; A61M 2205/3327; A61M 2205/3368; A61M 2205/36; A61M 2205/3633; A61M 2205/3646; A61M 2205/3653; A61M 2205/366; A61M 2205/3673; A61M 2210/12; A61M 5/14; A61M 5/44; A61M 5/445; H05B 1/0244; H05B 1/025
  See application file for complete search history.

(56) References Cited

U.S. PATENT DOCUMENTS

| 10,569,007 | B2 | 2/2020 | Hobro |
| 2005/0010157 | A1 | 1/2005 | Baraldi |
| 2013/0220907 | A1 | 8/2013 | Fulkerson |
| 2014/0050463 | A1 | 2/2014 | Theilacker-Beck |
| 2014/0221960 | A1* | 8/2014 | Stihler ................ H05B 1/0244 604/114 |
| 2017/0157310 | A1 | 6/2017 | Scarpaci |

FOREIGN PATENT DOCUMENTS

| JP | H1085323 | 4/1998 |
| JP | 2001353214 | 12/2001 |
| WO | WO 2005/072666 | 8/2005 |
| WO | WO 2012/155149 | 11/2012 |

OTHER PUBLICATIONS

Extended European Search Report for Application No. 18181135.7 dated Dec. 14, 2018 (6 pages).
Office Action issued in China for Application No. 201980044973.6 dated Aug. 30, 2023 (10 pages). English translation included.

\* cited by examiner

MEDICAL DEVICE FOR INTRODUCTION OF A FLUID INTO THE BLOOD CIRCULATION SYSTEM OF A PATIENT AND METHOD FOR CONTROLLING LEAKAGE CURRENTS IN A MEDICAL DEVICE PROVIDED OR COMBINED WITH A WARMING UNIT

This application is a U.S. National Stage Application of International Application No. PCT/EP2019/066878, filed Jun. 25, 2019, which was published in English on Jan. 9, 2020 as International Publication No. WO 2020/007666 A1. International Application No. PCT/EP2019/066878 claims priority to European Application No. 18181135.7 filed Jul. 2, 2018.

FIELD OF THE INVENTION

The present invention relates to a medical device for introduction of a fluid into the blood circulation system of a patient which is combined with, or comprises, a warming unit configured to warm the fluid before entering the blood circulation system of the patient. The warming unit may be part of the medical device or may be a separate device which is in communication with the medical device.

The invention also concerns a method for controlling leakage currents in medical device provided or combined with a warming unit.

In particular, the present invention relates to patient safety in the field of medical devices wherein the fluid flowing to the body of the patient is warmed to prevent hypothermia of the patient.

The medical device may be an extracorporeal blood treatment apparatus wherein blood and/or infusion/dialysis fluids is/are warmed. The medical device may also be a IV pole infusion device for intravenous infusions of medical fluids (e.g. saline, saline and drug, nutritional solution, or even blood for transfusion).

Background

In accordance with known solutions, blood warming units acting on the blood return line and capable of directly warming blood have been used.

In accordance with other solutions, patient's blood cooling is prevented by warming each of the infusion fluids prior to their infusion in the blood circuit or dialyzer.

Fluid/blood lines are passed through heat exchanger of a fluid/blood warming unit to achieve the required fluid or treated blood temperature before passing to the patient blood circulation. This heat exchanger is conductively in contact with fluid/blood line for efficient heat transfer.

For instance, during use of the warming unit, fluid flows in a plastic bag inserted into a heat exchanger of the warming unit to achieve the required fluid or blood temperature before passing to the patient blood circulation. The warming unit usually comprises heater elements powered by 230V/110V mains to heat the heat exchanger. An electrical insulator is placed between the heater elements and the heat exchanger to keep the heater elements close enough to heat exchanger for a better transfer of heat energy.

The dielectric material property of the mentioned electrical insulator forms a capacitance between the heater elements and the heat exchanger. Thus, the heater elements capacitive couple with fluid/blood path connected to patient, which disturbs other diagnostic devices connected to patient and also the organ structure, in particular the heart, which may be electrically stimulated. In other words, the warmed fluid/blood forms an electrically conductive path from the heat exchanger to the patient, bypassing the skin resistance. Through the electrical conductive path, leakage currents are conducted to the patient in contact with the fluid.

The mentioned warming units must comply with the high requirements for electrical safety of said fluid/blood warming units used in medicine and the strict safety standards of the international uniform classification "CF" (cardiac floating).

According to these standard, patient leakage currents, i.e., leakage currents conducted through a person in contact with the fluid, must not exceed a current magnitude of a total of 10 µA (microamperes) under normal conditions and 50 µA in case of a single fault, in which the patient is connected to the mains voltage of the warmer.

Systems for managing leakage currents under normal and single fault conditions in resistance based fluid warming systems are known.

For example, document US 2014/0050463 discloses a warmer having a resistance heating element with two electrical supply connection conductors having switches. A functional grounding conductor with switch is electrically conductively connected to heat transfer element. A sensor determines present magnitude of leakage current. A control device is structured to simultaneously switch all the switches into open switching state within defined time interval on occurrence of leakage current that is greater than or equal to the defined maximum threshold current magnitude. A resistor placed on the ground line between the heat transfer plates and the sensor is also disclosed.

The warming units of the prior art have some drawbacks.

In particular, the solution disclosed in document US 2014/0050463 stops heating the fluid on occurrence of leakage current that is greater than the defined maximum threshold current magnitude and this may imply problems for the patients.

SUMMARY OF THE INVENTION

In view of the above, it is an object of the present invention to propose a medical device (e.g. infusion device for intravenous infusions of medical fluids, extracorporeal blood treatment apparatus) provided with a warming unit which is able to assure safety and comfort of the patient.

It is an object of the present invention to propose a fluid warming unit for medical devices which is able to control leakage currents during the normal working condition and in case of single fault, in which the patient is connected to the mains voltage of the warming unit.

It is a further object of the present invention to propose a fluid warming unit for medical devices configured to provide heating also in case of single fault.

An object of the present invention is also to ensure that the fluid warming unit meets the relevant standard of the international safety CF classification to ensure a higher level of electrical safety.

It is a further object of the present invention to simplify the electronics and manufacturability of a fluid warming unit for medical devices.

It is a further object of the present invention to provide a fluid warming unit for medical devices which is reliable and cost effective.

At least one of the above objects is substantially achieved by connecting a heat transfer element of the fluid warming unit to a ground connection through a resistance element, which keeps a normal condition patient leakage current below a first limit value, and by disconnecting the heat transfer element from the ground connection if a current indicating that the patient is connected to the mains voltage is sensed through the resistance element, in order to keep a fault condition patient leakage current below a second limit value.

Aspects of the invention are disclosed in the following.

In accordance with a 1st independent aspect, a medical device for introduction of a fluid into the blood circulation system of a patient, comprises:
at least a fluid circuit configured to be coupled to a vascular access of the patient to introduce a fluid in the patient, wherein the fluid circuit presents a heated portion;
a warming unit coupled or configured to be coupled to the heated portion to warm the fluid before passing to the blood circulation system of the patient;
wherein the warming unit comprises:
at least an electrical heater element connected to a main electrical source providing a mains voltage,
at least a heat transfer element in contact or configured to be put in contact with the heated portion,
an electrical safety insulation interposed between the electrical heater element and the heat transfer element,
a ground connection connected to the heat transfer element,
a leakage current reduction circuit operatively interposed between the heat transfer element and the ground connection;
wherein the leakage current reduction circuit comprises:
a resistance element placed between the heat transfer element and the ground connection,
a current sense circuitry configured to sense a current through the ground connection.

In accordance with a 2nd independent aspect, a warming unit for a medical device comprises:
at least an electrical heater element connected to a main electrical source providing a mains voltage,
at least a heat transfer element in contact or configured to be put in contact with a heated portion of a fluid circuit of a medical device,
an electrical safety insulation interposed between the electrical heater element and the heat transfer element,
a ground connection connected to the heat transfer element,
a leakage current reduction circuit operatively interposed between the heat transfer element and the ground connection;
wherein the leakage current reduction circuit comprises:
a resistance element placed between the heat transfer element and the ground connection,
a current sense circuitry configured to sense a current through the ground connection.

In accordance with a 3rd independent aspect, it is provided a method for controlling leakage currents in a medical device provided or combined with a warming unit; wherein the warming unit comprises: at least an electrical heater element connected to a main electrical source providing a mains voltage, at least a heat transfer element in contact or configured to be put in contact with a heated portion of a fluid circuit of the medical device, an electrical safety insulation interposed between the electrical heater element and the heat transfer element, a ground connection connected to the heat transfer element.

In a 4th aspect according aspect 1 or 2, the leakage current reduction circuit is configured to perform the following procedure:
monitoring a current in the resistance element through the current sense circuitry and, if the monitored current is greater than a threshold current indicating that a patient is connected to the mains voltage, disconnecting the ground connection from the heat transfer element while keeping the electrical heater element connected to the main electrical source to keep heating;
trying to connect the ground connection to the heat transfer element every time interval while keeping heating, and, if the monitored current is lower than the threshold current, then keeping the ground connection connected to the heat transfer element, otherwise disconnecting again the ground connection from the heat transfer element and trying connecting again after said time interval.

In a 5th aspect according to aspect 1, 2 or 3, the leakage current reduction circuit is configured to perform the following procedure and/or the method comprises:
keeping leakage currents below a first limit value under normal working conditions of the warming unit in which the electrical heater element is connected to the main electrical source to perform heating;
keeping leakage currents below a second limit value under a fault condition of the warming unit in which a patient is connected to the mains voltage.

In a 6th aspect according to aspect 5, keeping the leakage currents below the first limit value comprises: connecting the main electrical source to the ground connection through a resistance element placed between the heat transfer element and the ground connection.

In a 7th aspect according to aspect 6, keeping the leakage currents below the second limit value comprises: disconnecting the ground connection from the heat transfer element, while keeping the electrical heater element connected to the main electrical source to keep heating.

In a 8th aspect according to aspect 7, comprising, after disconnecting the ground connection from the heat transfer element: trying to reconnect the ground connection to the heat transfer element every time interval until the fault condition is no longer present and while keeping the electrical heater element connected to the main electrical source to keep heating.

In a 9th aspect according to aspect 4 or 8, the time interval is comprised between 5 s and 15 s, optionally of 10 s.

In a 10th aspect according to aspect 5, the first limit value is comprised between 8 μA and 12 μA, optionally of 10 μA.

In a 11th aspect according to aspect 5 or 10, the second limit value is comprised between 45 μA and 55 μA, optionally of 50 μA.

In a 12th aspect according to aspect 1, 2, 4 or 6, the resistance element has a resistance comprised between 0.8 kOhm and 1.2 kOhm, optionally of 1 kOhm.

In a 13th aspect according to aspect 6, 7 or 8, it is provided to check if the warming unit is under a fault condition by monitoring a current flowing through the resistance element of the ground connection.

In a 14th aspect according to aspect 1, 2, 4, 6 or 12, if the current flowing through the resistance element is lower than a threshold current, the warming unit performs normal working conditions.

In a 15th aspect according to aspect 1, 2, 4, 6, 12 or 14, if the current flowing through the resistance element is higher than a threshold current, the warming unit is under the fault condition.

In a 16th aspect according to previous aspect 4, 14 or 15, the threshold current is comprised between +/−140 µA, optionally between +/−137 µA, optionally between +/−40 µA, optionally between +/−35 µA.

In a 17th aspect according to aspect 4, 7, 8 or 9, connecting or disconnecting the ground connection to/from the heat transfer element comprises: closing or opening an electrical operated switch placed between the heat transfer element and the ground connection.

In a 18th aspect according to aspect 1, 2, 4 or 5, the leakage current reduction circuit comprises an electrical operated switch configured to connect or disconnect the ground connection to/from the heat transfer element.

In a 19th aspect according to aspect 17 or 18, the electrical operated switch is a solid state relay.

In a 20th aspect according to aspect 17, 18 or 19, the resistance element is placed in series with the electrical operated switch between the heat transfer element and the ground connection.

In a 21st aspect according to any of aspects 1 to 20, the warming unit comprises a plurality of electrical heater elements. Optionally, the warming unit comprises two electrical heater elements, one for each transfer element. Optionally, when the ground connection is disconnected from the heat transfer element, the electrical heater elements are switched in parallel state.

In a 22nd aspect according to aspect 1, 2 or 4, the current sense circuitry comprises a differential amplifier configured to detect the current through the resistance element.

In a 23rd aspect according to aspect 22, the differential amplifier comprises two gain stages and a window comparator.

In a 24th aspect according to any of the previous aspects 1 to 23, the heated portion of the fluid circuit is a bag, optionally a plastic bag, optionally a soft bag, optionally a disposable bag.

In a 25th aspect according to any of the previous aspects 1 to 24, the warming unit comprises a casing delimiting a seat for the bag.

In a 26th aspect according to any of the previous aspects 1 to 25, the warming unit comprises two heat transfer elements placed on opposite sides of a seat to accommodate between them the bag. An electrical safety insulation is interposed between each electrical heater element and the respective heat transfer element. Optionally, the casing of the warming unit has a slot configured to insert the bag between the two heat transfer elements.

In a 27th aspect according to the previous aspect 26, the heat transfer elements are metal plates, optionally aluminum plates.

In a 28th aspect according to any of the previous aspects 1 to 27, the medical device is an infusion apparatus for intravenous infusions of medical fluids, like saline, saline and drug, nutritional solution or blood for transfusion.

In a 29th aspect according to the previous aspect 28, said infusion apparatus is a IV pole infusion apparatus.

In a 30th aspect according to the any of the previous aspects 1 to 27, the medical device is an extracorporeal blood treatment apparatus.

In a 31st aspect according to the previous aspect 30, the extracorporeal blood treatment apparatus comprises a blood treatment device and the fluid circuit; wherein the fluid circuit comprises: an extracorporeal blood circuit coupled to the blood treatment device and configured to be coupled to vascular accesses of the patient, a blood pump configured to be coupled to a pump section of the extracorporeal blood circuit.

In a 32nd aspect according to the previous aspect 31, the fluid circuit comprises a treatment fluid circuit operatively connected to the extracorporeal blood circuit and at least a fluid pump configured to be coupled to the treatment fluid circuit.

In a 33rd aspect according to the previous aspect 31 or 32, the extracorporeal blood circuit and/or the treatment fluid circuit present/s said heated portion.

The leakage current reduction circuit and/or the method allows to meet the patient leakage current limits under normal and single fault conditions. The leakage current reduction circuit and/or the method connect/s the heat transfer element to the protective ground connection through the resistance element in normal working conditions (no faults detected), which keeps the patient leakage current below the first limit value.

If a current is sensed through the resistance element, indicating the patient is connected to mains voltage, the electrical operated switch is opened, disconnecting the heat transfer element from the protective ground connection.

This keeps the patient leakage current under the second limit value which is the specified limit under the single fault condition (patient connected to mains). Heating remains active in this state.

The electrical operated switch is slowly turned back on every time interval, to determine if the patient is still connected to mains. If any current above the threshold current is measured, the electrical operated switch is immediately turned off. If a current below threshold current is detected, indicating the removal of the patient connected to mains fault condition, then the switch is fully turned on, connecting the heat transfer element to protective ground connection through the resistance element.

DESCRIPTION OF THE DRAWINGS

The following drawings relating to aspects of the invention are provided by way of non-limiting example.

DETAILED DESCRIPTION

Figure 1:
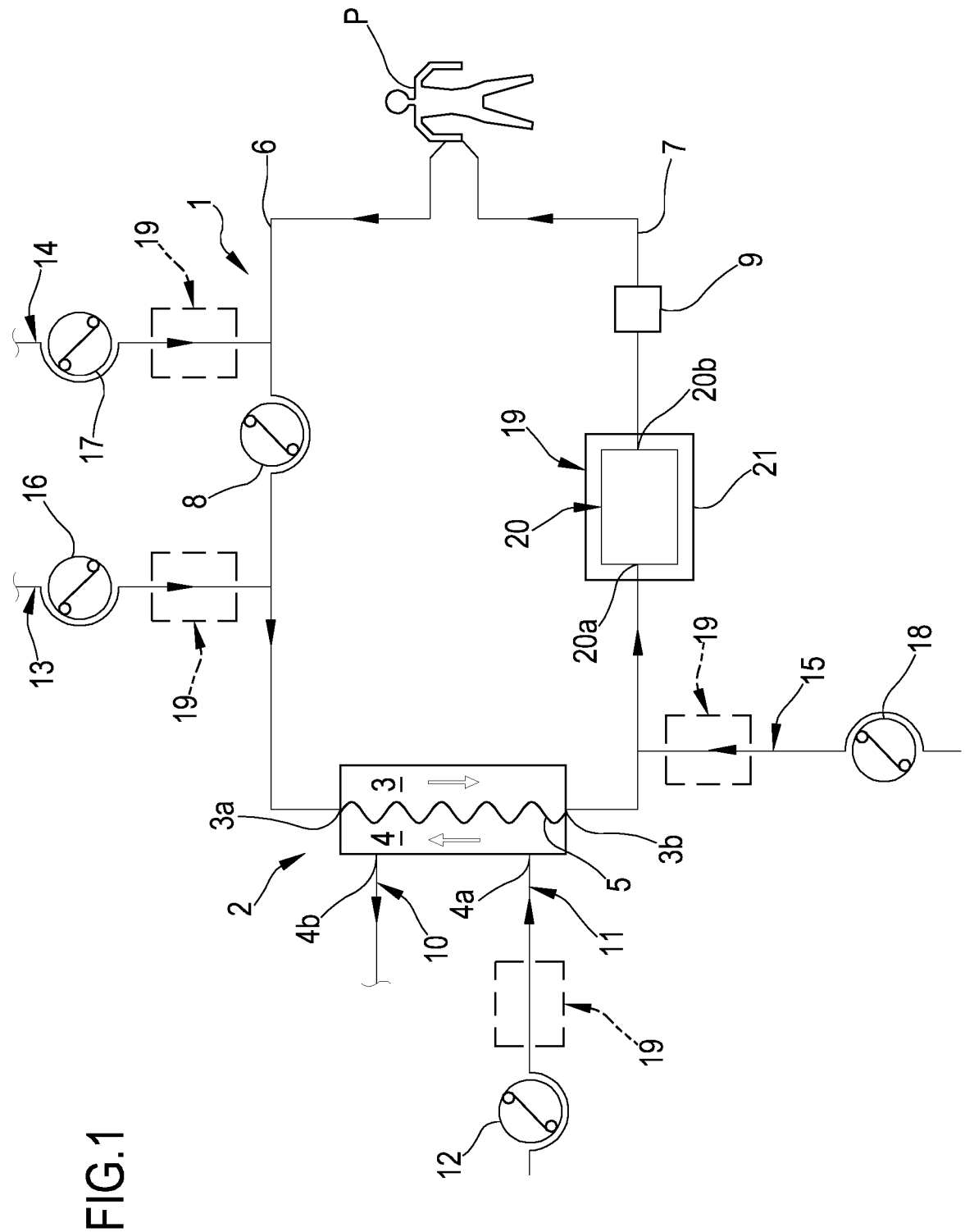
FIG. 1 shows a schematic representation of an extracorporeal blood treatment apparatus provided with a warming unit.

With reference to the appended drawings, FIG. 1 shows a schematic representation of an extracorporeal blood treatment apparatus 1.

The apparatus 1 comprises one blood treatment device 2, for example a hemofilter, a hemodiafilter, a plasmafilter, a dialysis filter or other unit suitable for processing the blood taken from a patient P.

The blood treatment device 2 has a first compartment or blood chamber 3 and a second compartment or fluid chamber 4 separated from one another by a semipermeable membrane 5. A blood withdrawal line 6 is connected to an inlet port 3a of the blood chamber 3 and is configured, in an operative condition of connection to the patient P, to remove blood from a vascular access device inserted, for example in a fistula on the patient P. A blood return line 7 connected to an outlet port 3b of the blood chamber 3 is configured to receive treated blood from the treatment unit 2 and to return the treated blood, e.g. to a further vascular access also connected to the fistula of the patient P. Note that various configurations for the vascular access device may be envisaged: for example, typical access devices include a needle or catheter inserted into a vascular access which may be a fistula, a graft or a central (e.g. jugular vein) or peripheral vein (femoral vein) and so on. The blood withdrawal line 6 and the blood return line 7 are part of an extracorporeal blood circuit of the apparatus 1.

The extracorporeal blood circuit 6, 7 and the treatment unit 2 are usually disposable parts which are loaded onto a frame of a blood treatment machine, not shown.

As shown in FIG. 1, the apparatus 1 comprises at least a first actuator, in the present example a blood pump 8, which is part of said machine and operates at the blood withdrawal line 6, to cause movement of the blood removed from the patient P from a first end of the withdrawal line 6 connected to the patient P to the blood chamber 3. The blood pump 8 is, for example, a peristaltic pump, as shown in FIG. 1, which acts on a respective pump section of the withdrawal line 6.

It should be noted that for the purposes of the present description and the appended claims, the terms "upstream" and "downstream" may be used with reference to the relative positions taken by components belonging to or operating on the extracorporeal blood circuit. These terms are to be understood with reference to a blood flow direction from the first end of the blood withdrawal line 6 connected to the patient P towards the blood chamber 3 and then from the blood chamber 3 towards a second end of the blood return line 7 connected to the vascular access of the patient P.

The apparatus 1 may further comprise an air trapping device 9 operating on the blood return line 7 (the air trapping device 9 is a venous deaeration chamber). The air trapping device 9 is placed online in the blood return line 7.

A first section of the blood return line 7 puts in fluid communication the outlet port 3b of the blood chamber 3 with the air trapping device 9 and a second section of the blood return line 7 puts in fluid communication the air trapping device 9 with the patient P. The blood coming from the blood chamber 3 of the treatment device 2 enters and exits the air trapping device 9 before reaching the patient P.

The apparatus 1 of FIG. 1 further comprises one fluid evacuation line 10 connected with an outlet port 4b of the fluid chamber 4 such as to receive the filtered waste fluid through the semipermeable membrane 5. The fluid evacuation line 10 receives such filtered waste fluid coming from the fluid chamber 4 of the treatment device 2, for example, comprising used dialysis liquid and/or liquid ultra-filtered through the membrane 5. The fluid evacuation line 10 leads to a receiving element, not shown, for example having a collection bag or a drainage pipe for the waste fluid. One or more dialysate pumps, not shown, may operate on the fluid evacuation line 10.

In the example of FIG. 1, a dialysis line 11 is also present for supplying a fresh treatment fluid into the inlet port 4a of the fluid chamber 4. The presence of this dialysis line 11 is not strictly necessary since, in the absence of the dialysis line 11, the apparatus 1 is still able to perform treatments such as ultrafiltration, hemofiltration or plasma-filtration. In case the dialysis line 11 is present, a fluid flow intercept device may be used, not shown, to selectively allow or inhibit fluid passage through the dialysis line 11, depending on whether or not a purification by diffusive effect is to be performed inside the treatment device 2.

The dialysis line 11, if present, is typically equipped with a dialysis pump 12 and is able to receive a fresh fluid from a module, not shown, for example a bag or on-line preparation section of dialysis fluid, and to send such a fluid to the inlet port 4a of the fluid chamber 4.

The fluid evacuation line 10, the dialysis line 11 and the fluid chamber 4 are part of a treatment fluid circuit.

The apparatus 1 as shown in FIG. 1 further comprises an infusion circuit comprising one or more infusion lines of a replacement fluid. According to the embodiment of FIG. 1, a pre-infusion line 13 is connected to the blood withdrawal line 6 between the blood pump 8 and the inlet port 3a of the blood chamber 3. A pre pump infusion line 14 is connected to the blood withdrawal line 6 upstream of the blood pump 8, between said blood pump 8 and the vascular access device inserted in the fistula on the patient P. A post-infusion line 15 is connected to the blood return line 7 upstream of the air trapping device 9. Each of the pre- and/or post-infusion lines 13, 14, 15 are provided with a respective pump 16, 17, 18. The pre- and/or post-infusion lines 13, 14, 15 may be supplied by fluid coming from bags or directly by infusion fluid prepared on-line. Each of the pre- and/or post-infusion lines 13, 14, 15 are part of the treatment fluid circuit.

The blood return line 7 presents a heated portion 19 in which blood is warmed before flowing into the blood circulation system of the patient P.

The heated portion 19 comprises a disposable soft plastic bag 20 presenting a bag inlet 20a for blood to be warmed and coming from the blood chamber 3 of the blood treatment device 2 and a bag outlet 20b for warmed blood flowing towards the air trapping device 9 and then into the patient P. The bag 20 is placed in a seat of a warming unit 21 which is schematically represented in FIG. 1.

In addition to or in place of the heated portion 19 for warming blood, the extracorporeal blood treatment apparatus 1 may comprise heated portions 19 in the treatment fluid circuit to warm treatment fluid. For instance, heated portions 19 (shown in dashed line in FIG. 1) may be present in the dialysis line 11, in the pre-infusion line 13, in the pre pump infusion line 14, in the post-infusion line 15. These heated portions 19 too may comprise a bag placed in a seat of a warming unit.

Figure 2:
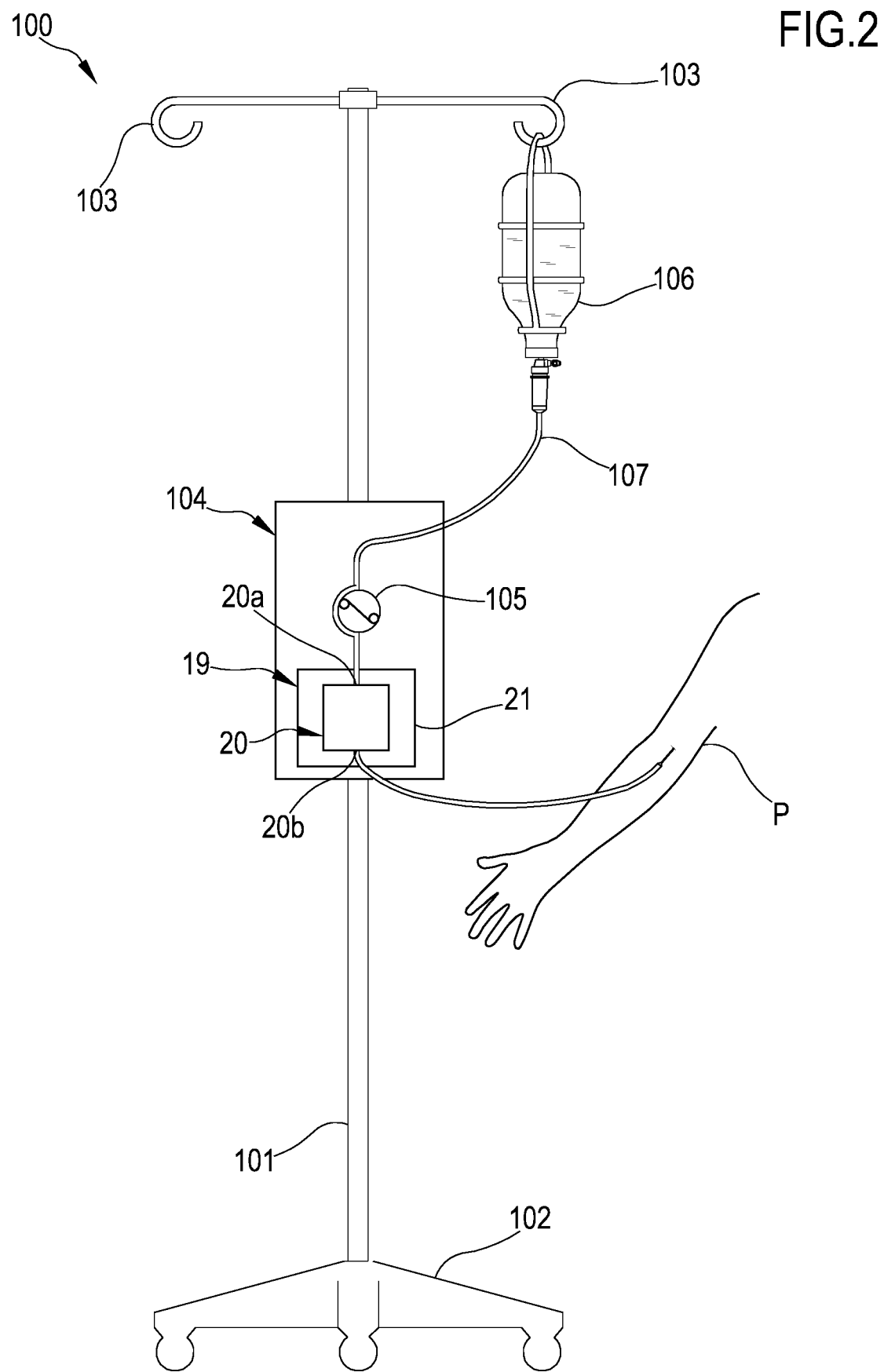
FIG. 2 shows a schematic representation of an infusion apparatus for intravenous infusions of medical fluids provided with a warming unit.

FIG. 2 shows a schematic representation of an infusion apparatus 100 for intravenous infusions of medical fluids (like saline, saline and drug, nutritional solution or blood for transfusion). The apparatus of FIG. 2 is a IV pole infusion device provided with a vertical pole 101, a base 102 with a plurality of caster wheels and two top hooks 103.

The vertical pole 101 carries an infusion device 104 provided with an infusion pump 105, for example a peristaltic pump and a control unit, not shown.

A container 106, like a flexible bag, for infusion fluid is suspended on one of the top hooks 103. A fluid line 107 departs from the infusion fluid container 106, goes through the infusion device 104 and presents a terminal end provided with a vascular access device inserted in the fistula on the patient P. The fluid line 107 is the fluid circuit configured to be coupled to the vascular access of the patient P.

Through the infusion device 104, the peristaltic infusion pump 105 acts on a respective pump section of the fluid line 107. When rotated, e.g., counter-clockwise, the infusion pump 105 causes a flow of infusion fluid along the fluid line 107 towards the patient P.

Downstream of the infusion pump 105, the fluid line 107 presents the heated portion 19 in which infusion fluid is warmed before flowing into the blood circulation system of the patient P.

The heated portion 19 comprises a plastic bag 20 presenting a bag inlet 20a for fluid to be warmed and coming from the infusion fluid container 106 and a bag outlet 20b for warmed fluid flowing towards the patient P. The bag 20 is placed in a seat of a casing of a warming unit 21 which is schematically represented in FIG. 2.

Figure 3:
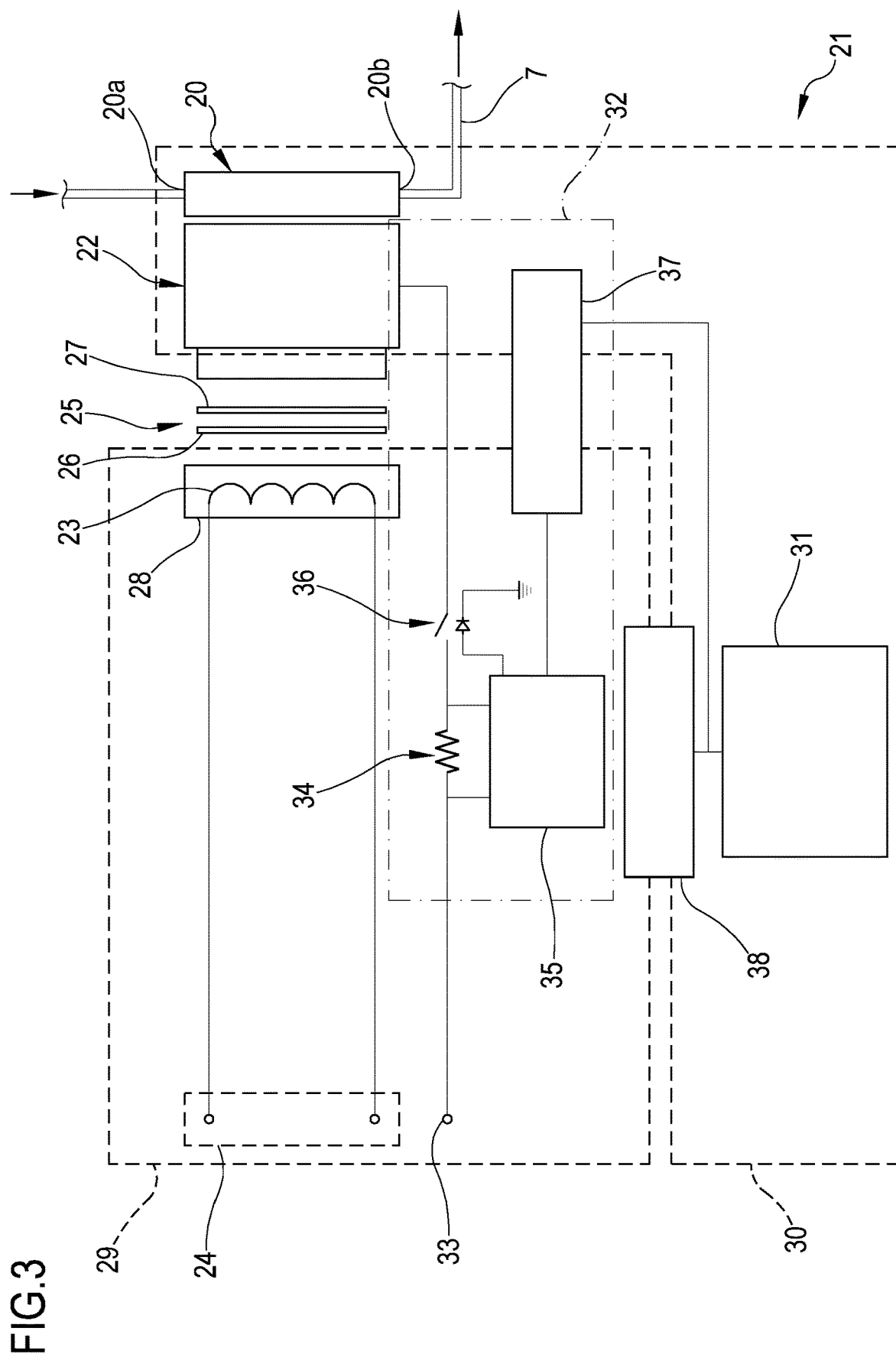
FIG. 3 shows a schematic representation of the warming unit of FIG. 1 or 2 with an embodiment of a circuitry according to the invention.
Figure 4:
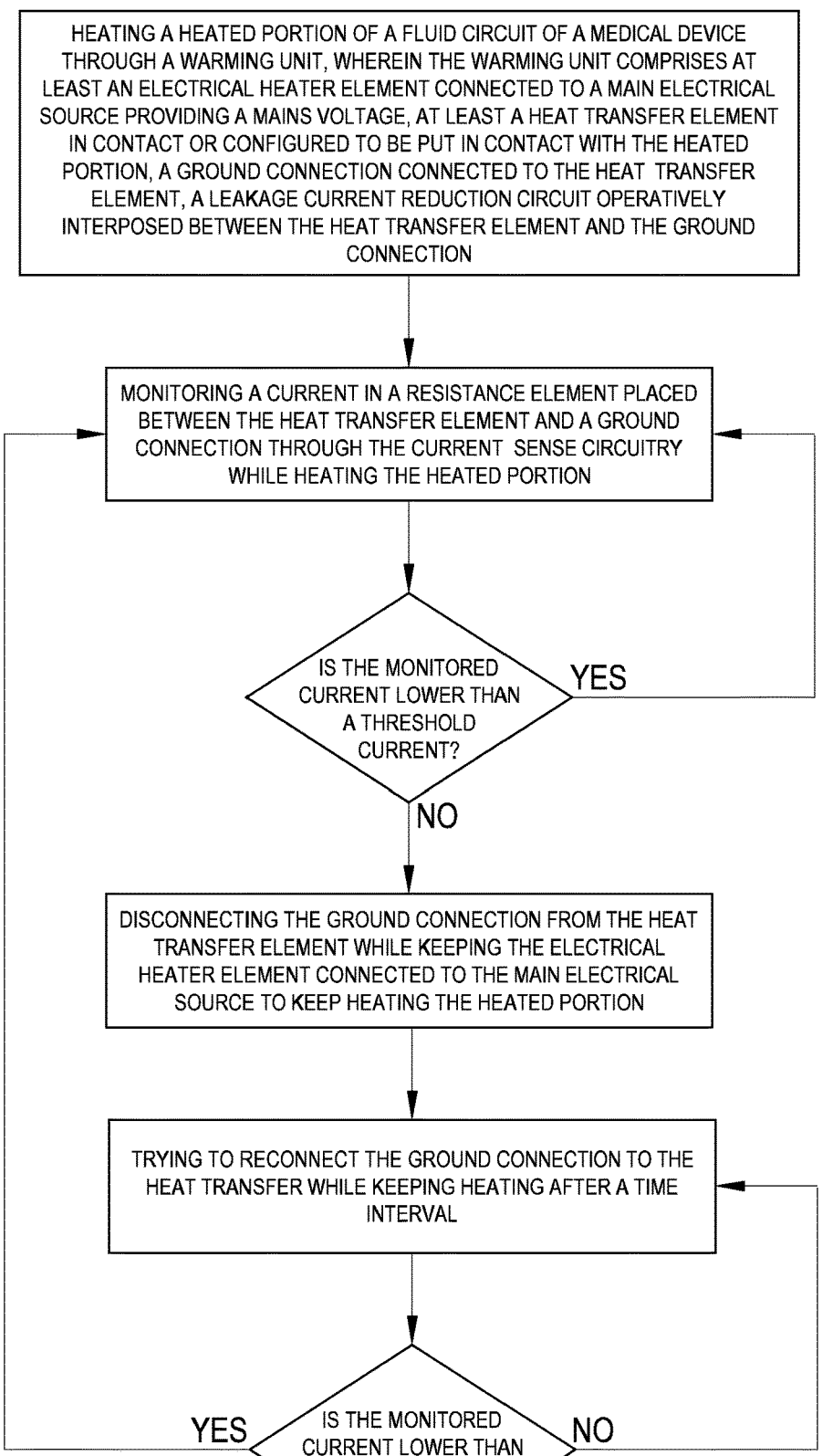
FIG. 4 shows a flow chart of a method for controlling leakage currents according to the invention.

FIG. 3 shows schematically a first embodiment of the warming unit 21 (which may be implemented in the extracorporeal blood treatment apparatus 1 of FIG. 1 or in the infusion apparatus 100 of FIG. 2) coupled to the bag 20 of the heated portion 19. Said heated portion 19 may be part of the blood return line 7 of the extracorporeal blood treatment apparatus 1 of FIG. 1 or may be part of the fluid line 107 of the infusion apparatus 100 of FIG. 2.

The warming unit 21 comprises a heat transfer element 22 shaped substantially like a metallic plate, optionally aluminum plate, having a first face 22a facing a face of the bag 20 which is substantially flat.

In some embodiments, the warming unit 21 comprises two heat transfer elements 22 shaped like two metallic plates parallel to each other and spaced one from the other to delimit the seat for the bag 20.

In some embodiments, the warming unit 21 comprises a casing which accommodates the two metallic plates delimiting the seat.

The casing has a slot configured to insert the bag 20 between the two metallic plates.

The heat transfer element or elements 22 is/are in contact or configured to be put in contact with the bag 20.

The warming unit 21 further comprises an electrical heater element 23 provided with one or more electric resistors and connected to a main electrical source 24 (200V or 110V, 50/60 Hz).

The main electrical source 24 applies to the electrical heater element 23 a mains voltage "V" to generate heat.

The electrical heater element 23 spreads over an area which is substantially equal to an area of the heat transfer element 22.

The main electrical source 24 is connected to the electrical heater element 23.

In some embodiments, the electrical heater element 23 comprises two electric resistors, each operatively coupled to a respective heat transfer element/metallic plate 22.

An electrical safety insulation 25 is interposed between the electrical heater element 23 and the heat transfer element 22. The electrical safety insulation 25 shown in FIG. 3 comprises a first and a second insulation layers 26, 27. Furthermore, the electrical heater element 23 is embedded in an insulation body 28.

A mains circuit 29 of the warming unit 21 comprises the electrical heater element 23 and the main electrical source 24.

A secondary circuit 30 of the warming unit 21 is isolated with respect to the mains circuit 29 and comprises the heat transfer element 22, the bag 20 and a warmer control circuitry 31 provided with a TRIAC control.

The warming unit 21 further comprises a leakage current reduction circuit 32 operatively interposed between the heat transfer element 22 and a protective ground connection 33.

The leakage current reduction circuit 32 comprises a resistance element 34 placed between the heat transfer element 22 and the protective ground connection 33, an electrical operated switch placed in series with the resistance element 34 and configured to connect or disconnect the ground connection 22 to/from the heat transfer element 22 and a current sense circuitry 35 configured to sense the current through the resistance element 34 and to command the electrical operated switch 36. In the embodiment shown in FIG. 3, the electrical operated switch 36 is a solid state relay and the resistance element 34 has a resistance of 1 kOhm.

In one embodiment, the current sense circuitry 35 comprises a differential amplifier comprising two gain stages and a window comparator configured to detect the current through the resistance element 34.

A first isolated power supply 37 and a second isolated power supply 38 are operatively interposed between the mains circuit 29 and the secondary circuit 30 to power the warmer control circuitry 31 and the leakage current reduction circuit 32. According to a method for controlling leakage currents, the leakage current reduction circuit 32 is configured to keep leakage currents below a first limit value (usually of 10 μA) under normal working conditions of the warming unit 21, in which the electrical heater element 23 is connected to the main electrical source 24 to perform heating, and to keep leakage currents below a second limit value (usually of 50 μA) under a fault condition of the warming unit 21 in which a patient P is connected to the mains voltage "V".

Under normal working conditions, the leakage currents are kept below the first limit value thanks to the resistance element placed between the heat transfer element 22 and the protective ground connection 33.

This connection steers parasitic heating currents through the heat transfer element and out the protective ground connection, which would normally flow through the patient, if the heat transfer element was not connected. These parasitic currents flow via capacitance between the electrical heater element to the heat transfer element, and capacitance between the heat transfer element to the patient fluid in the warming unit.

Meanwhile, a current in the resistance element 34 is monitored through the current sense circuitry 35.

If a current flowing through the resistance element 34 is lower than a threshold current "$i_t$" (e.g. of +/−137 μA), the warming unit 21 keeps performing normal working conditions.

If a current greater than the threshold current "$i_t$" is sensed through the resistance element 34, indicating the patient is connected to mains voltage "V" (fault condition of the warming unit 21), the electrical operated switch 36 is opened, disconnecting the heat transfer element 22 from the protective ground connection 33. When connected to ground and the heater elements fire, parasitic currents of 50 μA flow through the ground connection. Under minimum patient at MAINS conditions (90 VAC, low flow rates which creates minimum capacitive coupling) the minimum current we see through the plates is usually over 200 μA. So at 137 μA the circuit is usually guaranteed to trip.

The protective ground connection 33 is disconnected from the heat transfer element 22 but the electrical heater element 23 remains connected to the main electrical source 24 to keep heating.

Optionally, in this condition, the electrical heater elements 23 are switched into the parallel state, which allows the same amount of heating power to be delivered with ¼ of the TRIAC conduction time. The patient leakage current due to heating, while the heat transfer elements 22 are disconnected from protective ground connection 33, is proportional to the amount of time that the TRIACS are conducting.

This keeps the patient leakage current under the second limit value which is the specified limit under the single fault condition (patient connected to mains) while heating remains active in this state.

While the main electrical source 24 keeps heating, the electrical operated switch 36 is slowly turned back on every time interval "∆t" (e.g. of 10 s), to determine if the patient P is still connected to mains "V".

If any current above the threshold current "$i_t$" is measured, the electrical operated switch is immediately turned off. If a current below threshold current "$i_t$" is detected, indicating the removal of the patient P connected to mains "V" fault condition, then the electrical operated switch 36 is fully turned on, connecting the heat transfer element 22 to protective ground connection 33 through the resistance element 34 again.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and the scope of the appended claims.

The invention claimed is:

1. A medical device for introduction of a fluid into a blood circulation system of a patient, the medical device comprising:
   at least one fluid circuit configured to be coupled to a vascular access of the patient to introduce the fluid into the patient, wherein the at least one fluid circuit comprises a heated portion; and
   a warming unit coupled to the heated portion, the warming unit configured to warm the fluid before the fluid passes to the blood circulation system of the patient;
   wherein the warming unit comprises:
      at least one electrical heater element connected to a main electrical source providing a mains voltage,
      at least one heat transfer element in contact with the heated portion,
      an electrical safety insulation interposed between the at least one electrical heater element and the at least one heat transfer element,
      a ground connection connected to the at least one heat transfer element, and
      a leakage current reduction circuit operatively interposed between the at least one heat transfer element and the ground connection;
   wherein the leakage current reduction circuit comprises:
      a resistance element placed between the at least one heat transfer element and the ground connection, and
      a current sense circuitry configured to sense a current through the ground connection;
   wherein the leakage current reduction circuit is configured to:
      monitor a current in the resistance element through the current sense circuitry, and when the monitored current is greater than a threshold current indicating that the patient is connected to the mains voltage, disconnect the ground connection from the at least one heat transfer element while keeping the at least one electrical heater element connected to the main electrical source to continue warming the fluid,
      attempt to connect the ground connection to the at least one heat transfer element at a selected time interval after disconnecting the ground connection from the at least one heat transfer element while continuing to warm the fluid, and when the monitored current is lower than the threshold current, reconnect the ground connection to the at least one heat transfer element, and
      return to monitoring the current in the resistance element through the current sense circuitry after reconnecting the ground connection to the at least one heat transfer element.

2. The device of claim 1, wherein the resistance element has an electrical resistance comprised between 0.8 kOhm and 1.2 kOhm.

3. The device of claim 1, wherein the threshold current is comprised between +/−140 µA.

4. The device of claim 1, wherein the time interval is a time interval of 10 seconds.

5. The device of claim 1, wherein the leakage current reduction circuit comprises an electrically operated switch configured to connect and disconnect the ground connection and the at least one heat transfer element.

6. The device of claim 5, wherein the electrically operated switch is a solid state relay.

7. The device of claim 5, wherein the resistance element is placed in series with the electrically operated switch between the at least one heat transfer element and the ground connection.

8. The device of claim 1, wherein the leakage current reduction circuit is configured to:
   keep leakage currents below a first limit value under normal working conditions of the warming unit in which the at least one electrical heater element is connected to the main electrical source to perform heating; and
   keep leakage currents below a second limit value under a fault condition of the warming unit in which the patient is connected to the mains voltage.

9. The device of claim 8, wherein keeping the leakage currents below the first limit value comprises: connecting the main electrical source to the ground connection through the resistance element placed between the at least one heat transfer element and the ground connection.

10. The device of claim 8, wherein keeping the leakage currents below the second limit value comprises: disconnecting the ground connection from the at least one heat transfer element while keeping the at least one electrical heater element connected to the main electrical source to keep heating.

11. The device of claim 8, wherein the resistance element is placed in series with an electrically operated switch between the at least one heat transfer element and the ground connection.

12. The device of claim 1, wherein the at least one electrical heater element of the warming unit comprises a plurality of electrical heater elements, wherein when the ground connection is disconnected from the at least one heat transfer element, the plurality of electrical heater elements are switched in a parallel state.

13. The device of claim 1, wherein the current sense circuitry comprises a differential amplifier configured to detect the current through the resistance element.

14. The device of claim 13, wherein the differential amplifier comprises two gain stages and a window comparator.

15. The device of claim 1, wherein the heated portion of the at least one fluid circuit is a bag.

16. The device of claim 15, wherein the at least one heat transfer element of the warming unit comprises two heat transfer elements and the at least one electrical heater element of the warming unit comprises two electrical heater elements placed on opposite sides of a seat configured to accommodate the bag between the two heat transfer elements, the electrical safety insulation being interposed between each electrical heater element of the two electrical heater elements and each heat transfer element of the two heat transfer elements, wherein the warming unit comprises a slot configured to receive the bag between the two heat transfer elements.

17. A medical device for introduction of a fluid into a blood circulation system of a patient, the medical device comprising:
   at least one fluid circuit configured to be coupled to a vascular access of the patient to introduce the fluid into the patient, wherein the at least one fluid circuit comprises a heated portion; and
   a warming unit coupled to the heated portion, the warming unit configured to warm the fluid before the fluid passes to the blood circulation system of the patient;
   wherein the warming unit comprises:
      at least one electrical heater element connected to a main electrical source providing a mains voltage,
      at least one heat transfer element in contact with the heated portion,
      an electrical safety insulation interposed between the at least one electrical heater element and the at least one heat transfer element,
      a ground connection connected to the at least one heat transfer element, and
      a leakage current reduction circuit operatively interposed between the at least one heat transfer element and the ground connection;
   wherein the leakage current reduction circuit comprises:
      a resistance element placed between the at least one heat transfer element and the ground connection, and
      a current sense circuitry configured to sense a current through the ground connection;
   wherein the leakage current reduction circuit is configured to:
      keep leakage currents below a first limit value under normal working conditions of the warming unit in which the at least one electrical heater element is connected to the main electrical source to warm the fluid;
      keep leakage currents below a second limit value, higher than the first limit value, under a fault condition of the warming unit in which the patient is connected to the mains voltage;
   wherein keeping the leakage currents below the first limit value comprises: connecting the main electrical source to the ground connection through the resistance element placed between the at least one heat transfer element and the ground connection; and
   wherein keeping the leakage currents below the second limit value comprises: disconnecting the ground connection from the at least one heat transfer element while keeping the at least one electrical heater element connected to the main electrical source to continue warming the fluid.

18. A method for controlling leakage currents in a medical device, the medical device comprising:
   at least one fluid circuit configured to be coupled to a vascular access of a patient to introduce a fluid into the patient, wherein the at least one fluid circuit comprises a heated portion;
   a warming unit coupled to the heated portion to warm the fluid before the fluid passes to a blood circulation system of the patient;
   wherein the warming unit comprises:
      at least one electrical heater element connected to a main electrical source providing a mains voltage,
      at least one heat transfer element in contact with the heated portion of the at least one fluid circuit of the medical device,
      an electrical safety insulation interposed between the at least one electrical heater element and the at least one heat transfer element,
      a ground connection connected to the at least one heat transfer element, and
      a leakage current reduction circuit operatively interposed between the at least one heat transfer element and the ground connection;
   wherein the method comprises:
      keeping the leakage currents below a first limit value under normal working conditions of the warming unit in which the at least one electrical heater element is connected to the main electrical source to perform heating, and
      keeping the leakage currents below a second limit value, higher than the first limit value, under a fault condition of the warming unit in which the patient is connected to the mains voltage;
   wherein keeping the leakage currents below the first limit value comprises: connecting the main electrical source to the ground connection through a resistance element placed between the at least one heat transfer element and the ground connection; and
   wherein keeping the leakage currents below the second limit value comprises: disconnecting the ground connection from the at least one heat transfer element, while keeping the at least one electrical heater element connected to the main electrical source to continue warming the fluid.

19. The method of claim 18, comprising after disconnecting the ground connection from the at least one heat transfer element, attempting to reconnect the ground connection to the at least one heat transfer element at a selected time interval after disconnecting the ground connection from the at least one heat transfer element until the fault condition is no longer present and while keeping the at least one electrical heater element connected to the main electrical source to continue warming the fluid.

20. The method of claim 18, comprising checking if the warming unit is under the fault condition by monitoring a current flowing through the resistance element placed between the at least one heat transfer element and the ground connection.

21. The method of claim 20, wherein if the current flowing through the resistance element is lower than a threshold current, the warming unit warms the fluid.

22. The method of claim 20, wherein if the current flowing through the resistance element is higher than a threshold current between +/−140 µA, the warming unit is under the fault condition.

23. The method of claim 18, wherein connecting or disconnecting the ground connection to or from the at least one heat transfer element comprises: closing or opening an electrically operated switch placed between the at least one heat transfer element and the ground connection.

24. The method of claim 18, wherein the at least one electrical heater element of the warming unit comprises a plurality of electrical heater elements and the method comprises: switching the plurality of electrical heater elements in a parallel state when the ground connection is disconnected from the at least one heat transfer element.

* * * * *